US00PP15684P2

(12) United States Plant Patent
Iwaki

(10) Patent No.: US PP15,684 P2
(45) Date of Patent: Mar. 22, 2005

(54) ***TORENIA* PLANT NAMED 'SUNRENILAMU'**

(50) Latin Name: *Torenia hybrida*
Varietal Denomination: Sunrenilamu

(75) Inventor: Kazunari Iwaki, Ohmihachiman (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/328,010

(22) Filed: Dec. 26, 2002

(51) Int. Cl.[7] ..... A01H 5/00
(52) U.S. Cl. ..... Plt./263
(58) Field of Search ..... Plt./263

(56) References Cited

PUBLICATIONS

2002 "Flower & Green Catalog of Japan", 6 pages (Oct. 1, 2001).

*Primary Examiner*—Kent Bell
*Assistant Examiner*—Louanne Krawczewicz Myers
(74) *Attorney, Agent, or Firm*—Burns, Doane, Swecker & Mathis, LLP

(57) ABSTRACT

Disclosed herein is a *Torenia* plant having large flowers, vivid purple petals with a pale bluish-purple center and a vivid purple floral tube. The plant displays a semi-decumbent growth habit, medium branching and forms a great profusion of blooms. The entire plant remains in bloom for a considerable period of time. The plant grows and flowers well in shaded areas.

2 Drawing Sheets

Botanical/commercial classification: *Torenia hybrida*/*Torenia* Plant.

Varietal denomination: cv. 'Sunrenilamu'.

BACKGROUND OF THE VARIETY

The *Torenia* is a very popular plant and is used for flower bedding and potting in the summer season. There are only a few varieties of *Torenia* plants which have a semi-erect growth habit, medium branching, and a great profusion of blooms.

Accordingly, this invention is aimed at providing a new *Torenia* variety having large flowers, vivid purple flower petals with a pale bluish-purple center, a vivid purple floral tube, a semi-erect growth habit, medium branching, and a great profusion of blooms.

The new variety of *Torenia* plant according to this invention originated through the artificial chromosome doubling of the 'Sunrenimu' variety (U.S. Plant Pat. No. 10,120). During September 1998, cuttings of the 'Sunrenimu' variety were treated with 0.1% colchicines solution, and were propagated in a peat media by the use of cuttings at Yokaichi-shi, Shiga-ken, Japan. After two months, some surviving plantlets were transplated into pots. In December 1998, colchiploids were obtained from the cultivation. The discovered *Torenia* plant was propagated by the use of cuttings and was then grown in a bed and in pots where it was evaluated. The botanical characteristics of the plant were examined using the parent 'Sunrenimu' variety and the similar 'Sunrenilabu' variety (U.S. Plant Pat. No. 10,843) for comparison. As a result, it was concluded that this discovered *Torenia* plant is distinguishable from any other variety, whose existence is known to us.

Asexual propagation of the new variety at Aza-Iketani, Omori-cho, Yokaichi-shi, Shiga-ken, Japan, by the use of cuttings has confirmed that the new plant of the present invention is uniform and stable in its characteristics and reproduces true to type in succeeding generations.

This new variety of *Torenia* plant was named 'Sunrenilamu'.

In the following description, the color-coding is in accordance with The R.H.S. Colour Chart of The Royal Horticultural Society, London, England (2001). A color chart based on The Japan Color Standard for Horticultural Plants (J.H.S. Color Chart) is also added for reference.

The botanical characteristics of the 'Sunrenimu' variety parent are set forth hereafter.

Plant:

*Growth habit.*—Semi-erect. The stems hang down pliantly when potted in a hanging pot.

*Plant height.*—Approximately 10–20 cm.

*Plant width.*—Approximately 50–60 cm. The stems extend to a length of approximately 60 cm from the base.

*Growth.*—Medium branching with a great profusion of blooms and the entire plant remains in bloom for a considerable period of time.

*Blooming period.*—June to November in the southern Kanto area, Japan. The plant shape does not change throughout this period.

Stem:

*Diameter.*—Approximately 2.0 mm.

*Anthocyanin pigmentation.*—Present.

*Branching.*—Medium.

*Pubescence.*—Sparse.

*Length of internode.*—Approximately 6–8 cm.

Leaf:

*Phyllotaxis.*—Opposite.

*Shape of blade.*—Serrate.

*Length.*—Approximately 2.0–3.0 cm.

*Width.*—Approximately 1.5–2.5 cm.

*Depth of incision.*—Medium.

*Color (upper side).*—Moderate olive green (R.H.S. 137A, J.H.S. 3508).

*Pubescence of upper side.*—Sparse.

Flower:

*Facing direction.*—Laterally.

*Diameter.*—Approximately 2.0–3.0 cm.

*Height.*—Approximately 30–40 mm.

*Color of floral tube.*—Light purple (R.H.S. 92B, J.H.S. 8303).
*Color of petals.*—Single color; dark reddish-purple (R.H.S. 83B, J.H.S. 8909).
*Yellow eye color.*—Absent.
*Calyx.*—Approximately 1.5–2.0 cm in length.
*Anthocyanin pigmentation of calyx limb.*—Present.
*Peduncle.*—Approximately 1.5–2.0 mm in thickness; and approximately 2.0–3.0 cm in length.
*Reproductive organs.*—1 pistil and 4 stamens.
*Anther color.*—White.
*Flowering duration.*—Medium.

Physiological and ecological characteristics: Medium resistance to diseases and pests, high tolerance to heat and low tolerance to cold. The plant grows and flowers when shaded by trees.

The botanical characteristics of the 'Sunrenilabu' variety are set forth below.

Plant:
*Growth habit.*—Semi-erect.
*Plant height.*—Approximately 15–20 cm.
*Plant width.*—Approximately 60–80 cm.
Stem:
*Diameter.*—Approximately 1.5–2.0 mm.
*Anthocyanin pigmentation.*—Present.
*Branching.*—Medium.
*Pubescence.*—Sparse.
*Length of internode.*—Approximately 5–7 cm.
Leaf:
*Phyllotaxis.*—Opposite.
*Shape of blade.*—Serrate.
*Length.*—Approximately 2.5–3.5 cm.
*Width.*—Approximately 2.0–3.0 cm.
*Color.*—Moderate olive green (R.H.S. 137A, J.H.S. 3508).
*Pubescence.*—Sparse.
Flower:
*Facing direction.*—Laterally.
*Diameter.*—Approximately 3.0–4.0 cm.
*Height.*—Approximately 20–30 mm.
*Color of floral tube.*—Light purple (R.H.S. 85A, J.H.S. 8303).
*Color of petals.*—Bi-colored, upper petal: light purple (R.H.S. 85A, J.H.S. 8303), lower petal: deep purple (R.H.S. 84A, J.H.S. 8305), right and left side petals: vivid purple (R.H.S. 87A, J.H.S. 8306).
*Yellow eye color.*—Absent.
*Calyx.*—Approximately 2.0–2.5 cm in length.
*Anthocyanin pigmentation of calyx.*—Present.
*Reproductive organs.*—1 pistil and 4 stamens.
*Anther color.*—White.
*Flowering time.*—Medium.

Physiological and ecological characteristics: Medium resistance to diseases and pests, high tolerance to heat and low tolerance to cold. The plant grows and has flowers ordinarily in the shade of trees.

SUMMARY OF THE VARIETY

The new 'Sunrenilamu' variety displays large flowers, vivid purple flower petals with a pale bluish-purple center, a vivid purple floral tube, a semi-erect growth habit, medium branching, and a great profusion of blooms.

BRIEF DESCRIPTION OF THE DRAWINGS

The accompanying photographs show, as nearly true as it is reasonably possible to make the same in color illustrations of this character, typical specimens of the new cultivar. The plants were approximately three months of age and were being grown in greenhouses at Yokaichi-shi, Shiga-ken, Japan.

DESCRIPTION OF THE NEW VARIETY

Figure 1:
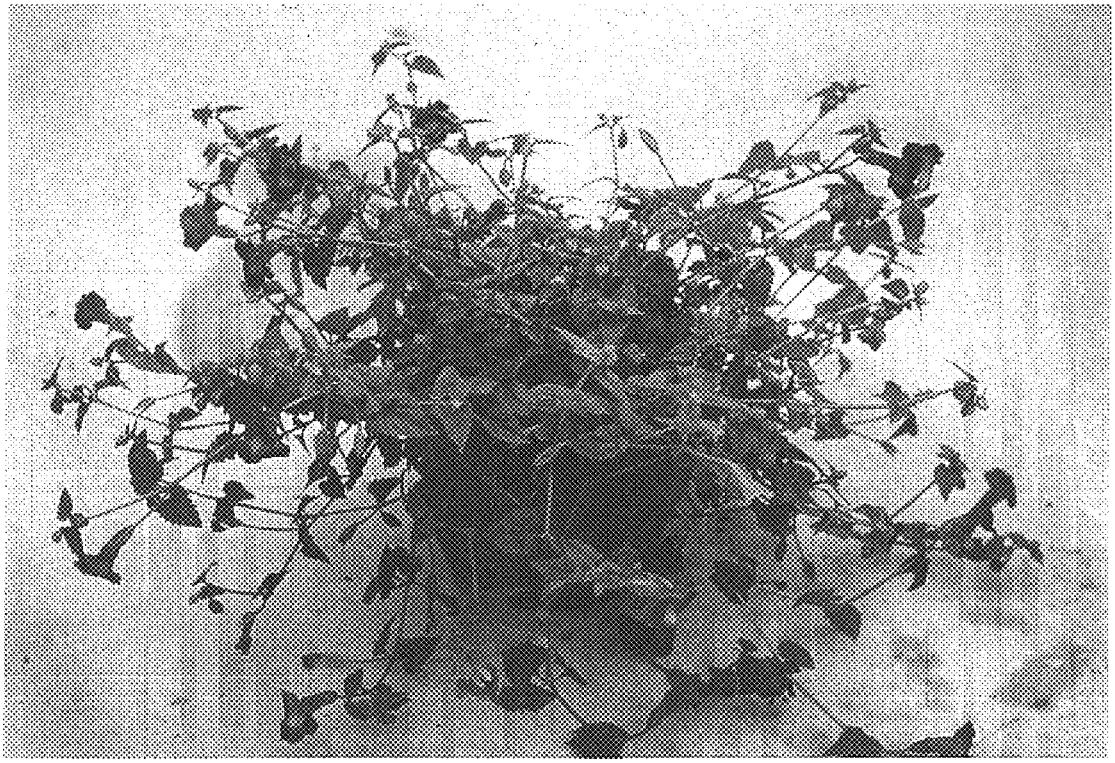
FIG. 1 is a photograph of a specimen of an entire plant of the new variety of the present invention while growing in a container.
Figure 2:
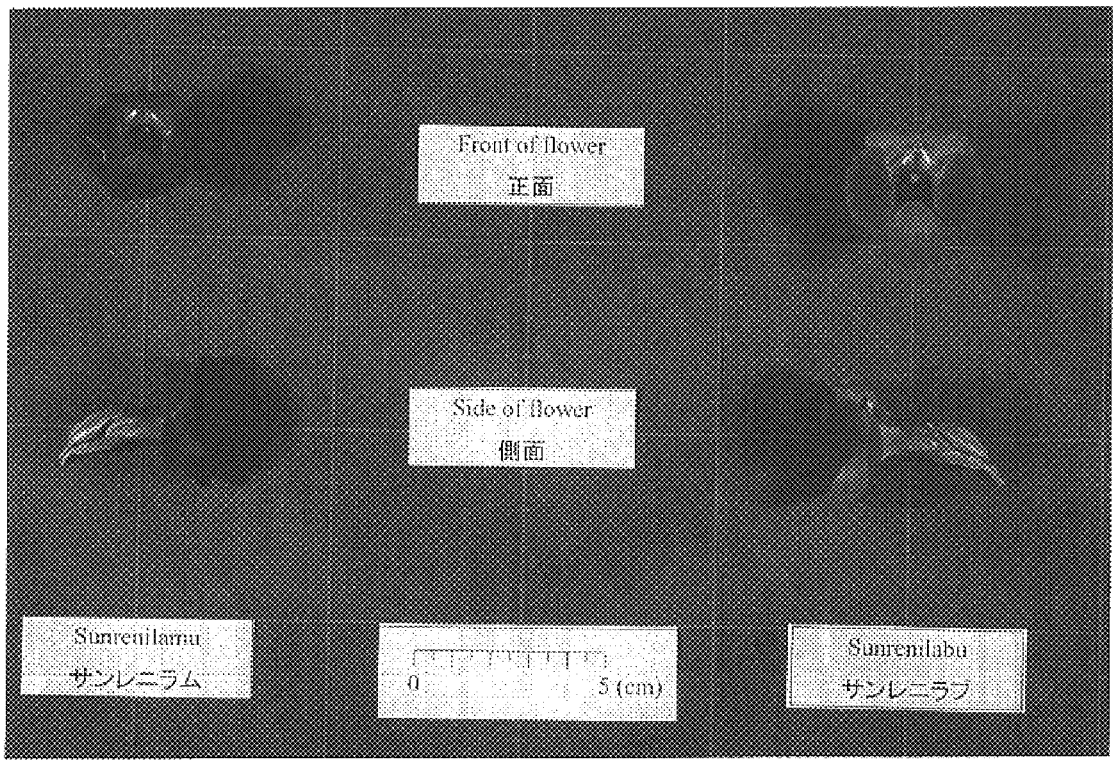
FIG. 2 is a photograph of specimens of flowers of the new variety of the present invention at the left and those of the 'Sunrenilabu' variety for comparison at the right.

The botanical characteristics of the new and distinct 'Sunrenilamu' variety are set forth hereafter. The plants were observed during August at Yokaichi-shi, Shiga-ken, Japan while growing in 24 cm containers in a greenhouse. The plants had been propagated by the use of stem cuttings and were approximately three months of age.

Plant:
*Growth habit.*—Semi-erect.
*Plant height.*—Approximately 27 cm.
*Plant width.*—Approximately 70 cm.
Stem:
*Length.*—Approximately 35 cm.
*Diameter.*—Approximately 2.4 mm.
*Anthocyanin pigmentation.*—Present, and light (near R.H.S. 60A).
*Branching.*—Medium.
*Pubescence.*—Sparse.
*Length of internode.*—Approximately 5.0 cm.
*Color.*—Near R.H.S. 144A.
Leaf:
*Shape of blade.*—Cordate.
*Apex.*—Acute.
*Base.*—Cordate.
*Margin.*—Serrate.
*Length.*—Approximately 3.0 cm.
*Width.*—Approximately 2.5 cm.
*Color (upper side).*—Dark green (R.H.S. 147A, J.H.S. 3716).
*Color (under side).*—Medium green (R.H.S. 147B).
*Pubescence of upper side.*—Sparse.
*Thickness of petiole.*—Medium (Approximately 1.5 mm).
*Length of petiole.*—Short (approximately 0.5 cm).
Flower:
*Inflorescence peduncles.*—Axillary.
*Peduncle color.*—R.H.S. 144A.
*Bud shape.*—Ellipsoidal.
*Bud length.*—Approximately 1.8 cm.
*Bud diameter.*—Approximately 1 cm.
*Bud texture.*—Pubescent.
*Bud color.*—R.H.S. 144B.
*Flowers on stem.*—Commonly 3.
*Bloom time.*—When planted in May outdoors, first blooms in June.
*Blooming frequency.*—Substantially continuously for approximately 6 months. Up to 200 or more blooms commonly are formed per plant.
*Fragrance.*—None.
*Flower form.*—Tubular and zygomorphic.

*Flower length.*—Medium to long, approximately 35 mm.

*Flower width.*—Medium to long, approximately 30 mm.

*Length of floral tube.*—Medium, approximately 35 mm.

*Color of floral tube.*—R.H.S. N87A on the outside and R.H.S. N87B on the inside.

*Petal number.*—Four and fused.

*Petal shape.*—Elliptic.

*Petal length.*—Approximately 1.2 cm for the upper petal, approximately 2 cm for the side petals at the left and right, and approximately 1.3 cm for the lower petal.

*Petal width.*—Approximately 2.7 cm for the upper petal, approximately 1 cm for the side petals at the left and right, and approximately 2.0 cm for the lower petal.

*Petal apex.*—Rounded.

*Petal base.*—Fused.

*Petal margin.*—Entire and undulated.

*Color of petals.*—On the upper surface R.H.S. N82A with R.H.S. 85B near the throat, and on the lower surface R.H.S. N87A.

*Yellow coloration of the petals.*—Absent.

*Vertical line on the petals.*—Present.

*Wave of upper bilabiate petal.*—Strong.

*Calyx shape.*—Deeply two-lobed.

*Calyx degree of development of wings.*—Medium.

*Calyx length.*—Short to medium (approximately 17 mm).

*Calyx color.*—R.H.S. 144A on both surfaces.

*Anthocyanin pigmentation of calyx.*—Absent.

*Anther color.*—The upper anthers are near R.H.S. N82A and the lower anthers are near R.H.S. 85B.

*Anthocyanin pigmentation of anther.*—Present and light.

*Anther number.*—Two pairs of fused anthers.

*Anther size.*—The upper anthers commonly are approximately 3 mm in length and approximately 1 mm in width, and the lower anthers commonly are approximately 5 mm in length and approximately 2 mm in width.

*Anther spur.*—Present.

*Filament color.*—Near R.H.S. 85D.

*Filament length.*—The upper filaments commonly are approximately 1.3 mm in length, and the lower filaments commonly are approximately 5 mm.

*Pollen.*—Sparse abortive pollen is observed that is near R.H.S. 150C in coloration.

*Pistil number.*—1.

*Stigma size.*—Approximately 3 mm×2 mm.

*Stigma color.*—Near R.H.S. N81C.

*Style length.*—Approximately 2.0 cm.

*Style color.*—Near R.H.S. N81C.

*Ovary size.*—Approximately 2×5 mm.

*Ovary color.*—R.H.S. 144A.

*Fruit.*—None observed.

*Seeds.*—None observed.

*Peduncle thickness.*—Medium, approximately 1.8 cm.

*Peduncle length.*—Short, approximately 1.5 cm.

*Flowering longevity.*—Approximately 3 days on the plant.

*Hardiness.*—Susceptible to damage under 5° C.

Physiological and ecological characteristics: Medium resistance to diseases and pests, high tolerance to heat, and low tolerance to cold.

This new variety 'Sunrenilamu' of *Torenia* plant is most suitable for growing in flower beds and pots, particularly in hanging baskets and planters.

It is claimed:

1. A new and distinct variety of *Torenia* plant, substantially as herein illustrated and described, characterized particularly as to novelty by (A) has a semi-decumbent growth habit with medium branching, (B) forms large flowers with a great profusion of blooms and the entire plant remaining in bloom for considerable period of time, (C) displays flower petals that are vivid purple with a pale bluish-purple center, (D) displays high resistance to heat, moderate resistance to diseases and pests and weak cold hardiness, and (E) grows and flowers well in shaded areas.

* * * * *